(12) United States Patent
Shin et al.

(10) Patent No.: US 9,474,706 B2
(45) Date of Patent: Oct. 25, 2016

(54) COMPOSITION FOR MAINTAINING EFFECT OF FILLER

(71) Applicant: AMOREPACIFIC CORPORATION, Seoul (KR)

(72) Inventors: Hyun Jung Shin, Yongin-si (KR); Jin Kyu Choi, Yongin-si (KR); Byung Gyu Kim, Yongin-si (KR); Dae Bang Seo, Yongin-si (KR); Sang Jun Lee, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/771,372

(22) PCT Filed: Feb. 27, 2014

(86) PCT No.: PCT/KR2014/001638
§ 371 (c)(1),
(2) Date: Aug. 28, 2015

(87) PCT Pub. No.: WO2014/133339
PCT Pub. Date: Sep. 4, 2014

(65) Prior Publication Data
US 2016/0000683 A1    Jan. 7, 2016

(30) Foreign Application Priority Data
Feb. 28, 2013 (KR) ......................... 10-2013-0022339

(51) Int. Cl.
| | | |
|---|---|---|
| A61K 8/65 | (2006.01) | |
| C07K 14/78 | (2006.01) | |
| A61Q 19/00 | (2006.01) | |
| A61Q 19/08 | (2006.01) | |
| A23L 1/305 | (2006.01) | |
| A61K 8/73 | (2006.01) | |

(52) U.S. Cl.
CPC ............... *A61K 8/65* (2013.01); *A23L 1/3053* (2013.01); *A61K 8/735* (2013.01); *A61Q 19/00* (2013.01); *A61Q 19/08* (2013.01); *A23V 2002/00* (2013.01); *A61K 2800/91* (2013.01)

(58) Field of Classification Search
CPC .... A61K 8/65; A61K 2800/91; A61K 8/735; A61Q 19/08; A61Q 19/00; A23V 2002/00; A23L 1/3053
See application file for complete search history.

(56) References Cited

U.S. PATENT DOCUMENTS

| | | | |
|---|---|---|---|
| 2011/0150846 A1* | 6/2011 | Van Epps | A61L 27/3839 424/93.7 |
| 2011/0160137 A1 | 6/2011 | Kim et al. | |
| 2012/0164116 A1 | 6/2012 | Van Epps | |

FOREIGN PATENT DOCUMENTS

| | | |
|---|---|---|
| CN | 101607982 | 12/2009 |
| KR | 1020070122315 | 12/2007 |
| KR | 102008010774 | 12/2008 |
| KR | 1020080109774 | 12/2008 |
| KR | 1020100025500 | 3/2010 |
| KR | 1020100101715 | 9/2010 |
| WO | 2007106457 | 9/2007 |
| WO | 2008002063 | 1/2008 |

OTHER PUBLICATIONS

Hyang Suk Jeong, et al., "Enhancement of Skin Immune Activation Effect of Collagen Peptides Isolated from Asterias amurensis", Korean J. Food Sci. Technol. vol. 40, No. 5, pp. 522-527 (2008), Abstract only.
Hyang Suk Jeong, et al., "Enhancement of Skin Immune Activation Effect of Collagen Peptides Isolated from Asterias amurensis", Korean J. Food Sci. Technol. vol. 40, No. 5, pp. 522-527 (2008).
International Search Report—PCT/KR2014/001638 dated Jun. 18, 2014.
Written Opinion—PCT/KR2014/001638 dated Jun. 18, 2014.

* cited by examiner

*Primary Examiner* — Julie Ha
*Assistant Examiner* — Li Ni Komatsu
(74) *Attorney, Agent, or Firm* — Cantor Colburn LLP

(57) ABSTRACT

The present invention relates to a composition for maintaining efficacy of a filler for a long period of time by containing collagen as an active ingredient. The composition according to the present invention is useful since the composition can promote the synthesis of hyaluronic acid and inhibit activity of hyaluronidase, thereby maintaining the efficacy of a hyaluronic acid filler for a longer period of time. Therefore, even with less number of times of filler injection, the efficacy of the filler can be maintained and skin irritation can be also reduced.

12 Claims, 3 Drawing Sheets

Control group 1

Test group 1

Control group 2

Test group 2

COMPOSITION FOR MAINTAINING EFFECT OF FILLER

TECHNICAL FIELD

The present disclosure relates to a composition containing collagen as an active ingredient, which maintains the effect of a filler for a long period of time.

BACKGROUND ART

A material implanted into living tissues should be non-toxic and, after the desired function has been achieved, degraded by metabolic activities and cleared out of the body. Recently, implantation of specific substances into the skin tissue for cosmetic purposes is increasing rapidly. Hyaluronic acid, which is commonly used for this purpose, is known to be metabolized and cleared out of the body within a few days after insertion or implantation regardless of the concentration or the type of the composition. To maintain the desired cosmetic effect for a long period of time, it is necessary to overcome the short period of metabolism of the hyaluronic acid in the human body. Therefore, needs on the development of a new filler material that can be maintained in the human body for months or longer are increasing.

The inventors of the present disclosure have confirmed that, when oral administration of collagen peptide is accompanied by injection of a hyaluronic acid filler, the collagen peptide can lengthen the in-vivo duration of the hyaluronic acid filler injected into the skin and have completed the present disclosure.

DISCLOSURE

Technical Problem

The present disclosure is directed to providing a composition that can maintain the effect of a hyaluronic acid filler for a long period of time after injection thereof.

Technical Solution

In an aspect, the present disclosure provides a composition for maintaining the effect of a hyaluronic acid filler which contains collagen as an active ingredient as well as a composition for promoting hyaluronic acid synthesis which contains collagen as an active ingredient.

Advantageous Effects

Since a composition according to the present disclosure can promote the synthesis of hyaluronic acid and inhibit the activity of hyaluronidase, it is useful in maintaining the effect of a hyaluronic acid filler for a longer period of time. As a result, the effect of the filler can be maintained even with a smaller number of filler injections and, thus, skin irritation can be reduced.

BEST MODE

Figure 1:
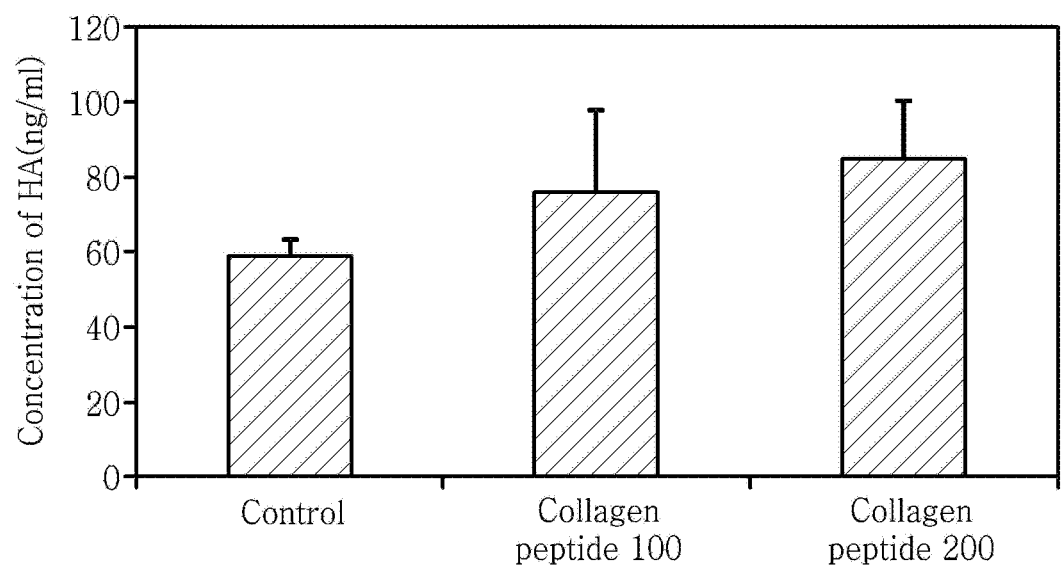
FIG. 1 shows increased synthesis of hyaluronic acid as a result of treatment with collagen peptide.

In an aspect, the present disclosure relates to a composition for maintaining the effect of a hyaluronic acid filler which contains collagen as an active ingredient.

Collagen is one of scleroproteins and contains a small amount of sugar. It is the main component of connective tissues and makes up about 30 wt % of the whole-body protein content in mammals. Collagen is present in the form of fibrils in the dermis, cartilage, etc. of animals and multiple collagen fibrils form into collagen fibers. The basic unit constituting the fiber is tropocollagen with a molecular weight of about 300,000, which is approximately 280 nm long and 1.5 nm in diameter.

The composition according to the present disclosure may maintain a hyaluronic acid filler more naturally for a longer period of time after being injected into the skin.

In another aspect, the present disclosure relates to a composition for promoting hyaluronic acid synthesis which contains collagen as an active ingredient.

The collagen peptide of the present disclosure may promote the synthesis of hyaluronic acid and may enhance the activity or quantity of enzymes or proteins involved in the synthesis of hyaluronic acid.

In the present disclosure, the 'hyaluronic acid filler' may mean a filler containing hyaluronic acid (HA) as a main ingredient. The hyaluronic acid is one of complex polysaccharides composed of amino acids and uronic acids, and is a polymer compound consisting of N-acetylglucosamine and glucuronic acid. The filler may mean a substitute material directly injected or inserted into the skin to fill wrinkles, depressed scars, etc. The filler may be used for various purposes without limitation, including alleviation of skin wrinkles, replenishment of moisture, or the like. The filler may be injected into the any part of the body, including, specifically, face, neck, etc.

In the present disclosure, 'to maintain the effect of a filler' may mean that the injected filler is degraded more slowly or that the content of hyaluronic acid which is the main ingredient of the filler is increased by promoting the synthesis of hyaluronic acid in vivo.

The composition of the present disclosure is useful since it can maintain the effect of a filler, including but not being limited to alleviation of skin wrinkles, replenishment of moisture, etc., for a long period of time. Specifically, it is advantageous in terms of skin irritation and economy since the filler injection period can be increased.

The composition according to the present disclosure may promote the synthesis of hyaluronic acid and may also promote the activity or increase the quantity of enzymes, proteins, etc. involved in the synthesis of hyaluronic acid.

In the composition according to the present disclosure, the collagen includes collagen peptide.

In the present disclosure, the collagen peptide is not particularly limited as long as it is a peptide having a molecular weight of 500-1,000 Da wherein amino acids are linked by peptide bonding. Specifically, the collagen peptide may include a Gly-X-Y collagen tripeptide, wherein X and Y may be any naturally occurring amino acids. The X and the Y may be the same or different amino acids.

The composition according to the present disclosure may contain 0.01-50 wt % of collagen peptide based on the total weight of the composition. Within this range, the composition may maintain the effect of the hyaluronic acid filler for a long period of time by promoting the synthesis of hyaluronic acid. In this aspect, the composition according to the present disclosure may contain the collagen peptide in an amount of 0.05-48 wt % based on the total weight of the composition, 0.1-46 wt % based on the total weight of the composition, 0.5-44 wt % based on the total weight of the composition, 1-42 wt % based on the total weight of the composition or 5-40 wt % based on the total weight of the composition.

In the composition according to the present disclosure, the collagen tripeptide may contain a Gly-X-Y collagen tripeptide.

In the composition according to the present disclosure, the X and the Y may be the same or different amino acids and the amino acid may be selected from a group consisting of glycine (Gly), alanine (Ala), valine (Val), leucine (Leu), isoleucine (Ile), threonine (Thr), serine (Ser), cysteine (Cys), methionine (Met), aspartic acid (Asp), asparagine (Asn), glutamic acid (Glu), glutamine (Gln), lysine (Lys), arginine (Arg), histidine (His), phenylalanine (Phe), tyrosine (Tyr), tryptophan (Trp) and proline (Pro).

Specifically, the collagen tripeptide may include glycine-proline-hydroxyproline, although not being limited thereto.

The composition according to the present disclosure may contain the collagen or the collagen peptide in an amount of 1-80 wt % based on the total weight of the composition. When the content of the collagen or the collagen peptide is less than 1 wt %, it is difficult to achieve the desired effect. And, when it exceeds 80 wt %, formulation may be difficult. In this aspect, the composition of the present disclosure may contain 1-80 wt %, 3-78 wt %, 5-76 wt %, 7-74 wt %, 9-72 wt %, 11-70 wt %, 13-68 wt %, 15-66 wt %, 17-64 wt % or 19-62 wt % of the collagen or the collagen peptide based on the total weight of the composition.

In the composition according to the present disclosure, the collagen or the collagen peptide may inhibit the activity of hyaluronidase. The collagen or the collagen peptide may inhibit the degradation of hyaluronic acid by inhibiting the activity of hyaluronidase or reducing its quantity. Accordingly, the synthesis of hyaluronic acid may be promoted and the effect of the filler may be maintained for a long period of time.

The composition according to the present disclosure may be a pharmaceutical composition.

The pharmaceutical composition according to the present disclosure may be prepared into a solid, semisolid or liquid formulation for oral administration by adding a commonly used inorganic or organic carrier to the active ingredient.

The formulation for oral administration may be a tablet, a pill, a granule, a capsule, a powder, a fine granule, a dust, an emulsion, a syrup, a pellet, etc. The active ingredient of the present disclosure may be easily prepared into the desired formulation according to a commonly employed method by using a surfactant, an excipient, a colorant, a flavoring agent, a preservative, a stabilizer, a buffer, a suspending agent or other commonly used adjuvants.

The pharmaceutical composition according to the present disclosure may be administered orally.

The dosage of the active ingredient will vary depending on the age, gender and body weight of a subject, particular disease or pathological condition to be treated and severity thereof, administration route or the discretion of a diagnoser. Determination of the dosage considering these factors is in the level of those skilled in the art. A general dosage is 0.001-2,000 mg/kg/day, more specifically 0.5-1,500 mg/kg/day.

The composition according to the present disclosure may also be a food composition.

In an aspect of the present disclosure, the food composition may be formulated into many forms including but not limited to a powder, a granule, a tablet, a capsule, a drink, etc.

If necessary, the food composition may contain one or more of the additives described below. The additive may be a concentrated fruit juice or a fruit juice powder of grape, apple, orange, lemon, pineapple, banana, pear, etc., a water-soluble or oil-soluble vitamin such as retinol palmitate, riboflavin, pyridoxine, cyanocobalamin, ascorbic acid, nicotinamide, calcium pantothenate, folic acid, biotin, cholecalciferol, choline bitartrate, tocopherol, β-carotene, etc., a flavor such as lemon flavor, orange flavor, strawberry flavor, grape flavor, vanilla essence, etc., an amino acid such as glutamic acid, sodium glutamate, glycine, alanine, aspartic acid, sodium aspartate, inosinic acid, etc., a nucleic acid or salts thereof, a plant fiber such as polydextrose, pectin, xanthan gum, glucomannan, alginic acid, etc., or a mineral such as sodium chloride, magnesium sulfate, potassium chloride, magnesium chloride, magnesium carbonate, calcium chloride, dipotassium phosphate, monosodium phosphate, calcium glycerophosphate, sodium ferrous citrate, ammonium ferric citrate, ferric citrate, manganese sulfate, copper sulfate, sodium iodide, potassium sorbate, zinc, manganese, copper, iodine, cobalt, etc.

In another aspect, the present disclosure provides a kit for injecting a filler, which contains a hyaluronic acid filler composition and the composition according to the present disclosure.

The kit according to the present disclosure may further contain an instruction which instructs that the hyaluronic acid is administered transdermally and the composition according to the present disclosure is administered orally.

The filler may be either applied on the skin so that it can be absorbed into the skin or may be inserted into the skin.

The kit of the present disclosure may be administered orally during or after the injection of a filler so as to prolong the duration of the effect of the filler.

In another aspect, the present disclosure may relate to a use of collagen for preparation of a composition for maintaining the effect of a hyaluronic acid filler. The use may include both therapeutic and non-therapeutic uses.

The present disclosure may also relate to a use of collagen for preparation of a composition for promoting hyaluronic acid synthesis. The use may include both therapeutic and non-therapeutic uses.

In the use for preparation of a composition for maintaining the effect of a hyaluronic acid filler or a composition for promoting hyaluronic acid synthesis according to the present disclosure, the collagen may include collagen peptide.

In the use for preparation of a composition for maintaining the effect of a hyaluronic acid filler or a composition for promoting hyaluronic acid synthesis according to the present disclosure, the composition may contain 0.01-50 wt % of collagen peptide based on the total weight of the composition. Within this range, the composition may maintain the effect of the hyaluronic acid filler for a long period of time by promoting the synthesis of hyaluronic acid. In this aspect, the composition according to the present disclosure may contain the collagen peptide in an amount of 0.05-48 wt % based on the total weight of the composition, 0.1-46 wt % based on the total weight of the composition, 0.5-44 wt % based on the total weight of the composition, 1-42 wt % based on the total weight of the composition or 5-40 wt % based on the total weight of the composition.

In the use for preparation of a composition for maintaining the effect of a hyaluronic acid filler or a composition for promoting hyaluronic acid synthesis according to the present disclosure, the collagen tripeptide may contain a Gly-X-Y collagen tripeptide.

In the use for preparation of a composition for maintaining the effect of a hyaluronic acid filler or a composition for promoting hyaluronic acid synthesis according to the present disclosure, the X and the Y may be the same or different amino acids and the amino acid may be selected from a group consisting of glycine (Gly), alanine (Ala), valine (Val), leucine (Leu), isoleucine (Ile), threonine (Thr), serine (Ser), cysteine (Cys), methionine (Met), aspartic acid (Asp), asparagine (Asn), glutamic acid (Glu), glutamine (Gln), lysine (Lys), arginine (Arg), histidine (His), phenylalanine (Phe), tyrosine (Tyr), tryptophan (Trp) and proline (Pro).

In the use for preparation of a composition for maintaining the effect of a hyaluronic acid filler or a composition for promoting hyaluronic acid synthesis according to the present disclosure, the X may be proline and the Y may be hydroxyproline.

In the use for preparation of a composition for maintaining the effect of a hyaluronic acid filler or a composition for promoting hyaluronic acid synthesis according to the present disclosure, the composition according to the present disclosure may contain the collagen or the collagen peptide in an amount of 1-80 wt % based on the total weight of the composition. When the content of the collagen or the collagen peptide is less than 1 wt %, it is difficult to achieve the desired effect. And, when it exceeds 80 wt %, formulation may be difficult. In this aspect, the composition of the present disclosure may contain 1-80 wt %, 3-78 wt %, 5-76 wt %, 7-74 wt %, 9-72 wt %, 11-70 wt %, 13-68 wt %, 15-66 wt %, 17-64 wt % or 19-62 wt % of the collagen or the collagen peptide based on the total weight of the composition.

In the use for preparation of a composition for maintaining the effect of a hyaluronic acid filler or a composition for promoting hyaluronic acid synthesis according to the present disclosure, the collagen or the collagen peptide may inhibit the activity of hyaluronidase.

In the use for preparation of a composition for maintaining the effect of a hyaluronic acid filler or a composition for promoting hyaluronic acid synthesis according to the present disclosure, the composition according to the present disclosure may be a pharmaceutical composition or a health food composition.

In another aspect, the present disclosure may relate to a method for maintaining the effect of a hyaluronic acid filler in a subject by administering a composition containing collagen to the subject. The subject includes one who is administered with the hyaluronic acid filler simultaneously with the administration of the composition or one who has been administered with the hyaluronic acid filler prior to the administration of the composition.

The present disclosure may also relate to a method for promoting hyaluronic acid synthesis in a subject by administering a composition containing collagen to the subject. The subject includes one who is administered with the hyaluronic acid filler simultaneously with the administration of the composition or one who has been administered with the hyaluronic acid filler prior to the administration of the composition.

In the method for maintaining the effect of a hyaluronic acid filler or the method for promoting hyaluronic acid synthesis according to the present disclosure, the collagen may include collagen peptide.

In the method for maintaining the effect of a hyaluronic acid filler or the method for promoting hyaluronic acid synthesis according to the present disclosure, the composition may contain 0.01-50 wt % of collagen peptide based on the total weight of the composition. Within this range, the composition may maintain the effect of the hyaluronic acid filler for a long period of time by promoting the synthesis of hyaluronic acid. In this aspect, the composition according to the present disclosure may contain the collagen peptide in an amount of 0.05-48 wt % based on the total weight of the composition, 0.1-46 wt % based on the total weight of the composition, 0.5-44 wt % based on the total weight of the composition, 1-42 wt % based on the total weight of the composition or 5-40 wt % based on the total weight of the composition.

In the method for maintaining the effect of a hyaluronic acid filler or the method for promoting hyaluronic acid synthesis according to the present disclosure, the collagen tripeptide may contain a Gly-X-Y collagen tripeptide.

In the method for maintaining the effect of a hyaluronic acid filler or the method for promoting hyaluronic acid synthesis according to the present disclosure, the X and the Y may be the same or different amino acids and the amino acid may be selected from a group consisting of glycine (Gly), alanine (Ala), valine (Val), leucine (Leu), isoleucine (Ile), threonine (Thr), serine (Ser), cysteine (Cys), methionine (Met), aspartic acid (Asp), asparagine (Asn), glutamic acid (Glu), glutamine (Gln), lysine (Lys), arginine (Arg), histidine (His), phenylalanine (Phe), tyrosine (Tyr), tryptophan (Trp) and proline (Pro).

In the method for maintaining the effect of a hyaluronic acid filler or the method for promoting hyaluronic acid synthesis according to the present disclosure, the X may be proline and the Y may be hydroxyproline.

In the method for maintaining the effect of a hyaluronic acid filler or the method for promoting hyaluronic acid synthesis according to the present disclosure, the composition according to the present disclosure may contain the collagen or the collagen peptide in an amount of 1-80 wt % based on the total weight of the composition. When the content of the collagen or the collagen peptide is less than 1 wt %, it is difficult to achieve the desired effect. And, when it exceeds 80 wt %, formulation may be difficult. In this aspect, the composition of the present disclosure may contain 1-80 wt %, 3-78 wt %, 5-76 wt %, 7-74 wt %, 9-72 wt %, 11-70 wt %, 13-68 wt %, 15-66 wt %, 17-64 wt % or 19-62 wt % of the collagen or the collagen peptide based on the total weight of the composition.

In the method for maintaining the effect of a hyaluronic acid filler or the method for promoting hyaluronic acid synthesis according to the present disclosure, the collagen or the collagen peptide may inhibit the activity of hyaluronidase.

In the method for maintaining the effect of a hyaluronic acid filler or the method for promoting hyaluronic acid synthesis according to the present disclosure, the composition according to the present disclosure may be a pharmaceutical composition or a health food composition.

Hereinafter, formulation examples of the composition of the present disclosure will be described. However, the following formulation examples are for illustrative purposes only and various formulations of a pharmaceutical composition and a health food composition are possible.

Formulation Example 1

Soft Capsule

According to a commonly employed method, 150 mg of the collagen peptide of Preparation Example 1, 2 mg of palm oil, 8 mg of hydrogenated palm oil, 4 mg of yellow beeswax and 6 mg of lecithin were mixed. Then, a soft capsule was prepared by filling 400 mg of the mixture per capsule.

Formulation Example 2

Tablet 150 mg of the collagen peptide of Preparation Example 1, 100 mg of glucose, 50 mg of red ginseng extract, 96 mg of starch and 4 mg of magnesium stearate were mixed. After forming granules by adding 40 mg of 30% ethanol, the granules were dried at 60° C. and then compressed into a tablet.

Formulation Example 3

Granule 150 mg of the collagen peptide of Preparation Example 1, 100 mg of glucose, 50 mg of red ginseng extract and 600 mg of starch were mixed. After forming granules by adding 100 mg of 30% ethanol, the granules were dried at 60° C. and then filled in a pouch. The final weight of the content was 1 g.

Formulation Example 4

Drink 150 mg of the collagen peptide of Preparation Example 1, 10 g of glucose, 50 mg of red ginseng extract, 2 g of citric acid and 187.8 g of purified water were mixed and filled in a bottle. The final volume of the content was 200 mL.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

Preparation Example 1

Preparation of Collagen Peptide

Collagen peptide used as the active ingredient in the present disclosure, which was purchased from Jellice (HATC, Jellice Co., Japan), contains 15% or more of a tripeptide such as glycine-proline-hydroxyproline.

Test Example 1

Ability of Promoting Synthesis of Hyaluronic Acid (HA) in Keratinocytes

Human-derived HaCaT keratinocytes (Dr N. E. Fusenig, Deutsches Krebsforschungszentrum, Heidelberg, Germany) were cultured in a DMEM medium containing 10% FBS under the condition of 37° C. and 5% $CO_2$. The cells were cultured on a 96-well plate. Upon reaching 80% confluence, the medium was replaced with an FBS-free medium and the cells were cultured for 24 hours. Subsequently, the cells were treated with the collagen peptide of Preparation Example 1, diluted 200-fold in PBS with a final concentration of 100 ppm or 200 ppm, and then cultured for 24 hours.

24 hours later, the medium was recovered and used for hyaluronic acid (HR) assay. The remaining cells were subjected to quantitative cell viability (CCK8) assay.

The CCK8 assay (Dojindo) and the hyaluronic acid assay (Echelon) were conducted according to the protocols of the kit manufacturers. The quantitated hyaluronic acid value was corrected by dividing with the cell viability value.

As a result, the collagen peptide-treated group showed 30-44% increased hyaluronic acid synthesis as compared to the untreated control group, as seen from FIG. 1. The promotion of the hyaluronic acid synthesis was proportional to the concentration of the collagen peptide. Accordingly, it was confirmed that the collagen peptide can promote the synthesis of hyaluronic acid in skin cells.

Test Example 2

Ability of Inhibiting Activity of Hyaluronidase

The effect of inhibiting the activity of hyaluronidase was investigated to confirm whether the hydrolysis of hyaluronic acid which is the main ingredient of the filler is inhibited.

20 μL of the collagen peptide was added to 50 μL of a 0.1 M hyaluronidase solution (7,900 units/mL), to a final concentration of 0.2, 0.4, 0.6, 0.8 or 1.0 mg/mL. After mixing with 200 μL of 12.5 mM $CaCl_2$ to activate the enzyme, incubation was performed in an aqueous solution at 37° C. for 20 minutes. For the control group, distilled water was added instead of the collagen peptide and incubation was performed for 20 minutes in an aqueous solution. After adding 250 μL of a 0.1 M hyaluronic acid solution (12 mg/5 mL) to the hyaluronidase solution activated with $Ca^{2+}$, incubation was performed again in an aqueous solution for 40 minutes. After the incubation, 100 μL of a 0.4 N NaOH solution and 100 μL of 0.4 M potassium tetraborate were added to the reaction mixture and then cooled after incubation in a boiling water bath for 3 minutes. After adding 3.28 mL of a dimethylaminobenzaldehyde solution (a mixture of 4 g of p-dimethylamino-benzaldehyde, 350 mL of 100% acetic acid and 50 mL of 10 N HCl) to the cooled reaction mixture and incubating in a water bath at 37° C. for 20 minutes, absorbance was measured at 585 nm.

As can be seen from Table 1, the collagen peptide exhibited superior effect of inhibiting the activity of hyaluronidase. The effect was dependent on the concentration of the collagen peptide.

TABLE 1

| | Concentration of collagen peptide (mg/mL) | | | | |
|---|---|---|---|---|---|
| | 0.2 | 0.4 | 0.6 | 0.8 | 1.0 |
| Inhibition of hyaluronidase activity (%) | 30.4 | 32.8 | 48.6 | 75.2 | 82.4 |

Test Example 3

Ability of Maintaining Hyaluronic Acid Filler in Living Tissues

After injecting a commercially available hyaluronic acid filler (Glytone II, AmorePacific, 20 mg/g HA) into the back of hairless mice, the duration of volume in the skin was observed.

15- to 17-week-old hairless mice were divided into two groups. One group was given a normal diet (control groups)

and the other group was orally administered with 500 mg/kg collagen peptide for 3 weeks (test groups). The control groups and the test groups were subdivided as described in Table 2 by varying the injection volume of the filler.

TABLE 2

| | Filler injection volume |
|---|---|
| Control group 1 | 0.02 mL |
| Control group 2 | 0.04 mL |
| Test group 1 | 0.02 mL |
| Test group 2 | 0.04 mL |

Figure 2:
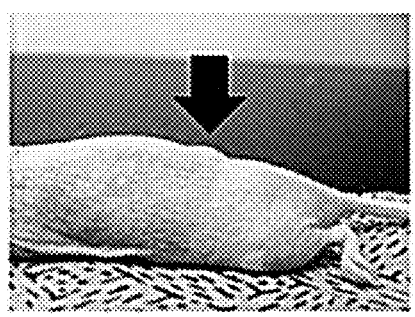
FIG. 2 shows photographs showing volume change after injection of a filler as a result of treatment with collagen peptide.
Figure 2:
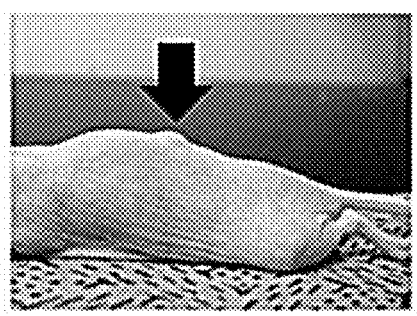
Figure 2:
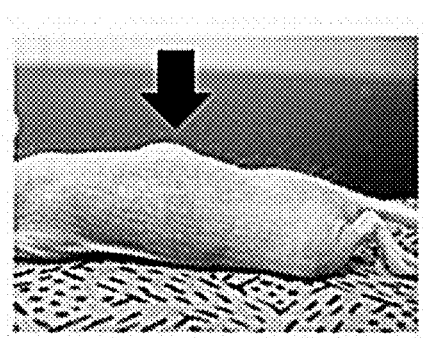
Figure 2:
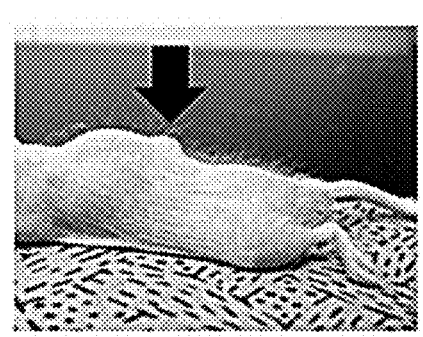
Figure 3:
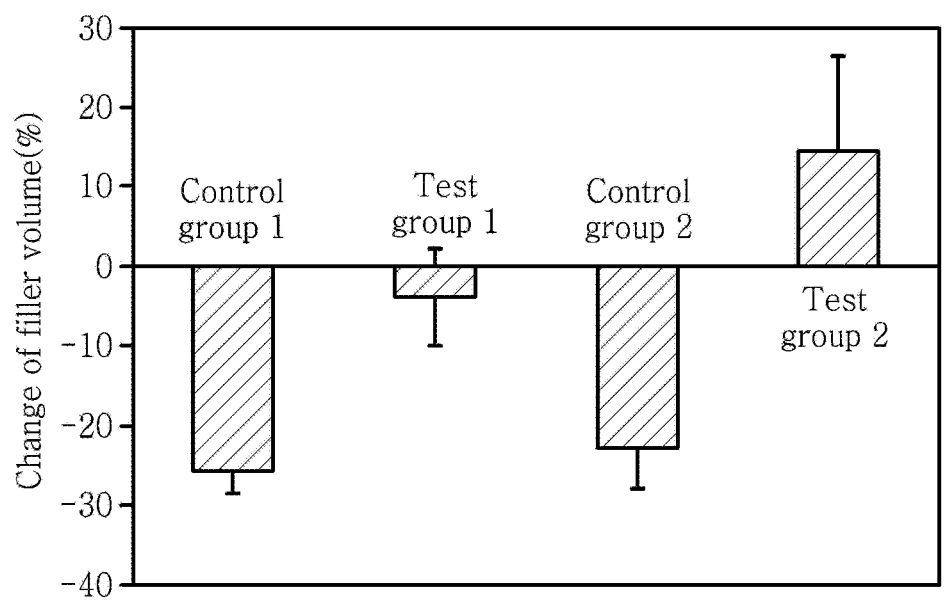
FIG. 3 shows a graph showing volume change after injection of a filler as a result of treatment with collagen peptide.

After filler injection, both the control groups and the test groups were given a normal diet and only the test groups were orally administered with the collagen peptide. Then, the volume change of the control groups and the test groups was observed for 4 weeks. As can be seen from FIG. 2 and FIG. 3, the control groups showed faster and consistently decreasing volume of the filler. In contrast, the test groups which were orally administered with the collagen peptide showed superior effect of maintaining the volume as compared to the control groups.

While some aspects of the present disclosure have been described in detail, it will be obvious to those skilled in the art that the detailed description is provided only as specific embodiments and the scope of the present disclosure is not limited thereby. Accordingly, the substantial scope of the present disclosure will be determined by the appended claims and their equivalents.

INDUSTRIAL APPLICABILITY

Since a composition according to the present disclosure can promote the synthesis of hyaluronic acid and inhibit the activity of hyaluronidase, it is useful in maintaining the effect of a hyaluronic acid filler for a longer period of time. As a result, the effect of the filler can be maintained even with a smaller number of filler injections and, thus, skin irritation can be reduced.

The invention claimed is:

1. A method for maintaining the filling effect of a hyaluronic acid filler comprising
administering a composition comprising an effective amount of collagen or collagen peptide to a subject in need thereof, wherein the composition is administered after a hyaluronic acid filler is administered to the subject, and
wherein the collagen or collagen peptide maintains the filling effect of the hyaluronic acid filler.

2. The method according to claim 1, wherein the composition comprises collagen peptide.

3. The method according to claim 2, wherein the composition comprises 0.01-50 wt % of the collagen peptide based on the total weight of the composition.

4. The method according to claim 2, wherein the collagen peptide comprises a Gly-X-Y collagen tripeptide, and wherein each of X and Y is a naturally occurring amino acid.

5. The method according to claim 4, wherein the X and the Y are the same or different amino acids and the amino acid is selected from the group consisting of glycine (Gly), alanine (Ala), valine (Val), leucine (Leu), isoleucine (Ile), threonine (Thr), serine (Ser), cysteine (Cys), methionine (Met), aspartic acid (Asp), asparagine (Asn), glutamic acid (Glu), glutamine (Gln), lysine (Lys), arginine (Arg), histidine (His), phenylalanine (Phe), tyrosine (Tyr), tryptophan (Trp), proline (Pro) and hydroxyproline.

6. The method according to claim 4, wherein the X is proline and the Y is hydroxyproline.

7. The method according to claim 1, wherein the composition comprises 1-80 wt % of collagen or collagen peptide based on the total weight of the composition.

8. The method according to claim 1, wherein the collagen or the collagen peptide inhibits the activity of hyaluronidase.

9. The method according to claim 1, wherein the composition is a pharmaceutical composition.

10. The method according to claim 1, wherein the composition is a food composition.

11. The method according to claim 1, wherein the composition comprises 1-80 wt % of collagen based on the total weight of the composition.

12. The method according to claim 1, wherein the composition is administered orally.

* * * * *